(12) United States Patent
Pollard et al.

(10) Patent No.: US 8,674,087 B2
(45) Date of Patent: Mar. 18, 2014

(54) PROCESSES FOR ISOLATION AND PURIFICATION OF ENFUMAFUNGIN

(75) Inventors: Jennifer M. Pollard, Monroe, NJ (US); Rebecca A. Chmielowski, Clark, NJ (US); Lisa M. Dietrich, Granville, OH (US); Francis P. Gailliot, Cranford, NJ (US); Kent Goklen, West Conshohocken, PA (US)

(73) Assignee: Scynexis, Inc., Durham, NC (US)

( * ) Notice: Subject to any disclaimer, the term of this patent is extended or adjusted under 35 U.S.C. 154(b) by 61 days.

(21) Appl. No.: 13/393,638

(22) PCT Filed: Aug. 30, 2010

(86) PCT No.: PCT/US2010/047104
§ 371 (c)(1),
(2), (4) Date: Mar. 1, 2012

(87) PCT Pub. No.: WO2011/028654
PCT Pub. Date: Mar. 10, 2011

(65) Prior Publication Data
US 2012/0165513 A1 Jun. 28, 2012

Related U.S. Application Data

(60) Provisional application No. 61/239,517, filed on Sep. 3, 2009.

(51) Int. Cl.
*C07H 1/08* (2006.01)

(52) U.S. Cl.
USPC ............................................. 536/127; 536/5

(58) Field of Classification Search
USPC ............................................. 536/127, 128, 5
See application file for complete search history.

(56) References Cited

U.S. PATENT DOCUMENTS

| | | | |
|---|---|---|---|
| 3,658,649 A | 4/1972 | Arnold et al. | |
| 4,189,568 A | 2/1980 | Johnson et al. | |
| 5,756,472 A * | 5/1998 | Liesch et al. | 514/27 |

FOREIGN PATENT DOCUMENTS

| | | |
|---|---|---|
| WO | 2007-126900 A2 | 11/2007 |
| WO | 2007-127012 A1 | 11/2007 |
| WO | 2009-045311 A1 | 4/2009 |

OTHER PUBLICATIONS

Chmielowski et al., "Optimization of a Crystallization Process to Produce a High Purity Secondary Metabolite Intermediate", AIChE (American Institute of Chemical Engineers) Annual Meeting, Nov. 2007, meeting abstract.
Dietrich et al., "Isolation and Purification of a Pharmaceutically Active Secondary Metabolite via Solids Phase Extraction.", AIChE Annual Meeting, Nov. 2005, meeting abstract.
Onishi et al., "Discovery of Novel Antifungal (1,3)-beta-D-Glucan Synthase Inhibitors", Antimicrobial Agents and Chemotherapy, 2000, vol. 44, No. 2, pp. 368-377.
Pelaez et al., "The Discovery of Enfumafungin, A Novel Antifungal Compound Produced by an Endophytic Hormonema Species Biological Activity and Taxonomy of the Producing Organisms", Systematic and Applied Microbiology, 2000, vol. 23, pp. 333-343.
Pollard et al., "Optimization of Whole Broth Extraction: A Case Study of Secondary Metabolite Isolation", AIChE Annual Meeting, Nov. 2006, meeting abstract.
Russotti et al., "Development of a Pilot Scale Fungal Fermentation Process for the Production of a Secondary Metabolite: A Case Study". ACS (American Chemical Society) National Meeting, Mar. 2004, meeting abstract.
Russotti et al., "Development of Pilot Scale Fermentation Processes to Support Pre-clinical Material Demands", ACS National Meeting, Mar. 2005, meeting abstract.
Schwartz, "Cell Wall Active Antifungal Agents", Expert Opinion Therapeutic Patents, 2001, vol. 11, No. 11 pp. 1761-1772.
Schwartz et al., "Isolation and Structural Determination of Enfumafungin, A Triterpene Glycoside Antifungal Agent That is a Specific Inhibitor of Glucan Synthesis", J Amer Chem Soc, 2000, vol. 122, pp. 4882-4886.

* cited by examiner

*Primary Examiner* — Elli Peselev

(57) ABSTRACT

The present disclosure relates to processes useful in the isolation and purification of enfumafungin, which is classified as a triterpene glycoside antifungal compound and acts as a glucan synthase inhibitor. Enfumafungin has application in the treatment of conditions caused by fungal infection and is also useful as an intermediate in the preparation of other compounds useful as antifungal agents and/or inhibitors of (1,3)-β-D-glucan synthesis.

20 Claims, 2 Drawing Sheets

PROCESSES FOR ISOLATION AND PURIFICATION OF ENFUMAFUNGIN

FIELD OF THE INVENTION

The present invention relates to processes useful in the isolation and purification of enfumafungin, which is classified as a triterpene glycoside antifungal compound and acts as a glucan synthase inhibitor. Enfumafungin is useful in the treatment of conditions caused by fungal infection and is also useful as an intermediate in the preparation of other compounds useful as antifungal agents and/or inhibitors of (1,3)-β-D-glucan synthesis.

BACKGROUND OF THE INVENTION

Fungal infection is a major healthcare problem, and the incidence of hospital-acquired fungal diseases continues to rise. Severe systemic fungal infection in hospitals (such as candidiasis, aspergillosis, histoplasmosis, blastomycosis and coccidioidomycosis) is commonly seen in neutropaenic patients following chemotherapy and in other oncology patients with immune suppression, in patients who are immune-compromised due to Acquired Immune Deficiency Syndrome (AIDS) caused by HIV infection, and in patients in intensive care. Systemic fungal infections cause about 25% of infection-related deaths in leukaemics. Infections due to Candida species are the fourth most important cause of nosocomial bloodstream infection. Serious fungal infections may cause 5 to 10% of deaths in patients undergoing lung, pancreas or liver transplantation. Treatment failures are still very common with all systemic mycoses. Secondary resistance also arises. Thus, there remains an increasing need for effective new therapy against mycotic infections and for processes for isolating and purifying compounds useful in such therapy.

Enfumafungin is a hemiacetal triterpene glycoside that is produced in fermentations of a *Hormonema* spp. associated with living leaves of *Juniperus communis*. See U.S. Pat. No. 5,756,472; Fernando Peláez et al., *The Discovery of Enfumafungin, a Novel Antifungal Compound Produced by an Endophytic Hormonema Species Biological Activity and Taxonomy of the Producing Organisms*, 23 SYSTEM. APPL. MICROBIOL. 333 (2000); Robert E. Schwartz et al., *Isolation and Structural Determination of Enfumafungin, a Triterpene Glycoside Antifungal Agent That Is a Specific Inhibitor of Glucan Synthesis*, 122 J. AM. CHEM. SOC. 4882 (2000); Robert E. Schwartz, *Cell wall active antifungal agents*, 11(11) EXPERT OPIN. THER. PATENTS 1761 (2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase. See J. Onishi et al., *Discovery of Novel Antifungal (1,3)-β-D-Glucan Synthase Inhibitors*, 44(2) ANTIMICROBIAL AGENTS AND CHEMOTHERAPY 368 (2000); Pelaez et al., *Systematic and Applied Microbiology*, 23:333-343, 2000). 1,3-β-D-Glucan synthase remains an attractive target for antifungal drug action because it is present in many pathogenic fungi that affords broad antifungal spectrum and because there is no mammalian counterpart. As such, these compounds have little or no mechanism-based toxicity.

Because of the desirability of glycan synthase inhibitors as antifungal agents, there is a need for cost-effective processes for isolating and purifying enfumafungin and other natural products, both for use as antifungal agents and/or glycan synthase inhibitors and for use as intermediates for the preparation of other compounds that can be used as antifungal agents and/or glycan synthase inhibitors.

SUMMARY OF THE INVENTION

The present invention relates to a process that is useful in the isolation and purification of enfumafungin, which is useful as an antifungal agent and/or glycan synthase inhibitor. The present invention also encompasses processes that afford intermediates useful in the production of antifungal agents and/or glycan synthase inhibitors. The processes of the present invention afford advantages over previously known procedures because the claimed processes produce high-purity enfumafungin (formula I below).

DETAILED DESCRIPTION OF THE INVENTION

Figure 1:
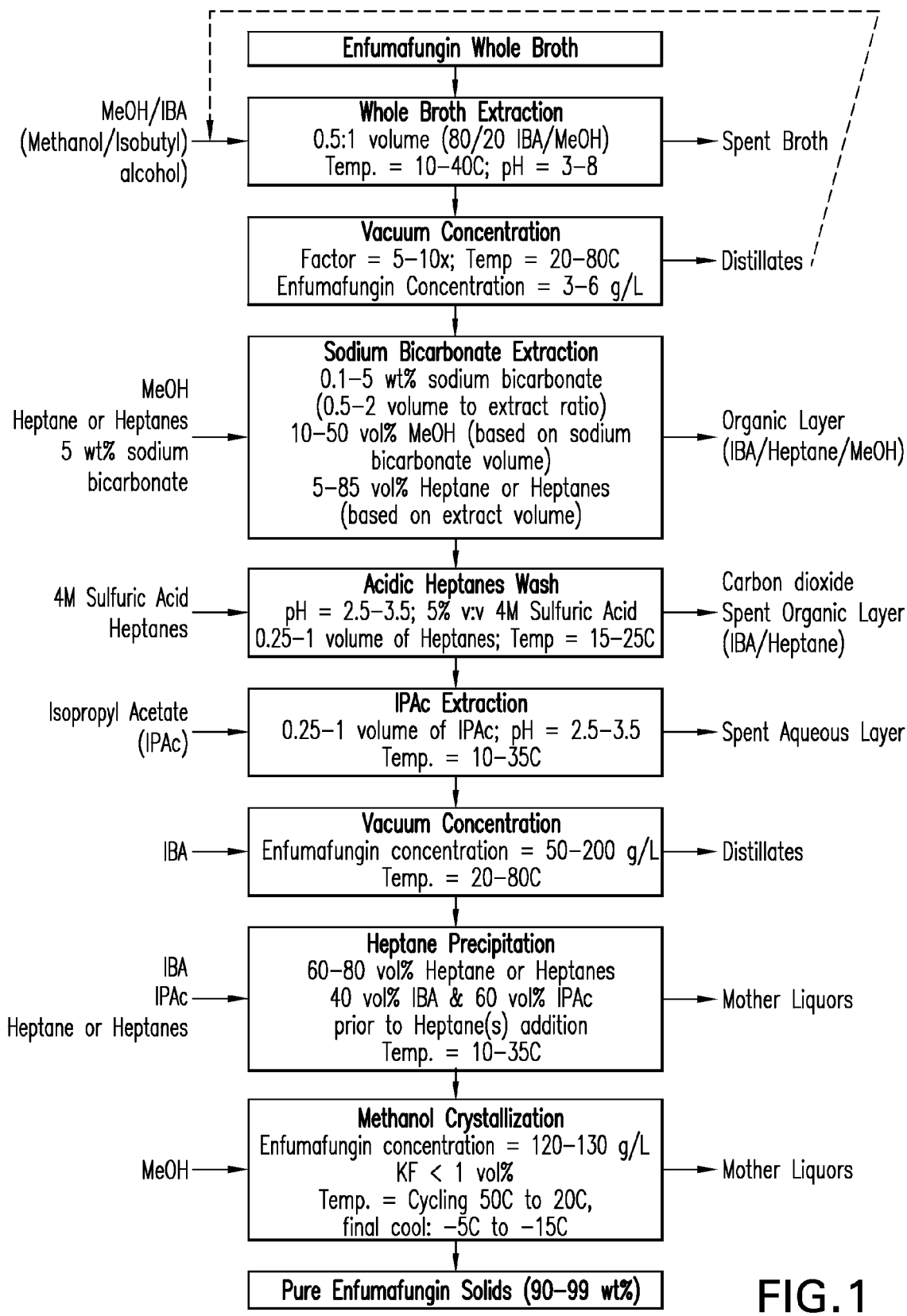
FIG. 1 is a flow-chart showing a process according to aspects of the first embodiment of the invention.
Figure 2:
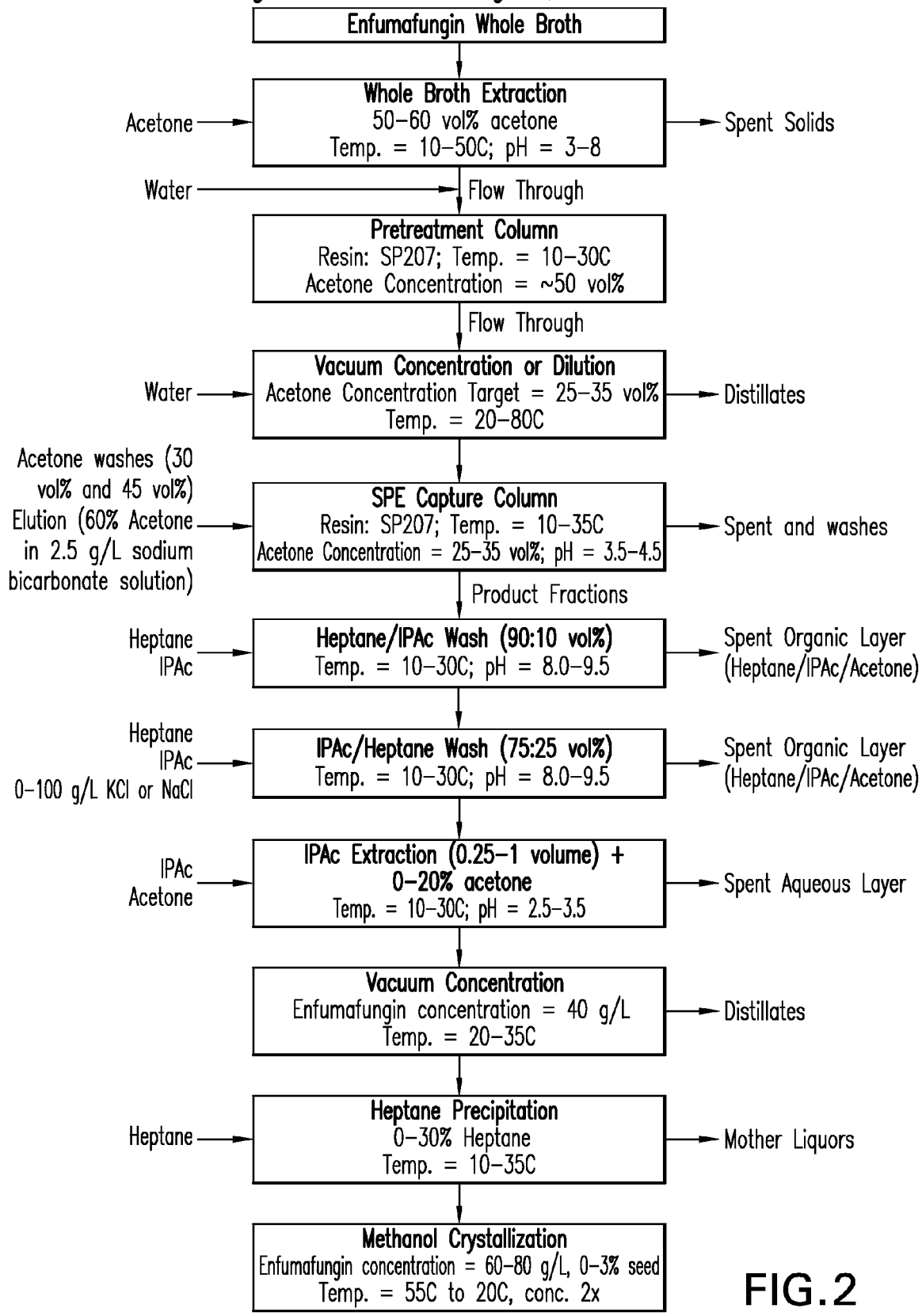
FIG. 2 is a flow-chart showing a process according to aspects of the second embodiment of the invention.

A first embodiment of the invention relates to a process for isolating a compound of formula I:

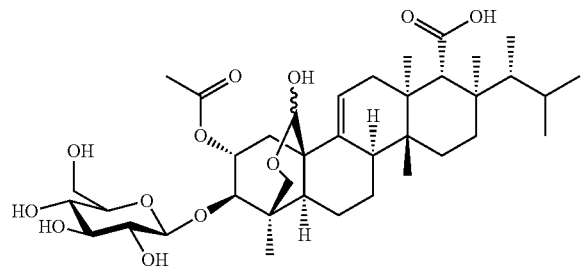

the process comprising:

a) performing solvent extraction on a fermentation broth comprising cells containing a compound of formula I to produce an organic liquid containing the compound of formula I;

b) concentrating the organic liquid containing the compound of formula I;

c) performing solvent extraction on the concentrated liquid to produce aqueous layer $A^1$ containing the compound of formula I;

d) adjusting the pH of aqueous layer $A^1$;

e) adding heptane to aqueous layer $A^1$ and removing the heptane layer;

f) performing solvent extraction on aqueous layer $A^1$ to produce organic layer $O^2$ containing the compound of formula I and aqueous layer $A^2$;

g) concentrating organic layer $O^2$ to produce a concentrated layer containing the compound of formula I;

h) precipitating the compound of formula I from the concentrated layer; and i) crystallizing the precipitated compound of formula I.

In a first aspect of the first embodiment, step a) is performed using a combination solvent consisting of 100 to about 75 percent by volume of a main solvent and 0 to about 25 percent by volume of a co-solvent; said main solvent chosen from the group consisting of methyl ethyl ketone, isobutanol, ethyl acetate and isopropyl acetate, and said co-solvent chosen from the group consisting of methanol, ethanol, isopropanol, acetone and acetonitrile. In particular aspects of this embodiment, said step a) is performed at a pH in a range of from about 3 to about 8 and a temperature in a range of from about 10° C. to about 40° C. In this aspect of the first embodiment, all other steps are as described in the general process of the embodiment.

In a second aspect of the first embodiment, step b) comprises concentrating the extract to a concentration that is from about 5 to about 25 times an initial concentration, but resulting in no greater than a product concentration of about 10 g/L. In this aspect of the first embodiment, all other steps are as described in the general process of the embodiment or in the first aspect of this embodiment.

In a third aspect of the first embodiment, step c) is performed adding bicarbonate solution, methanol and heptane. In particular instances of this aspect, the bicarbonate solution comprises about 5 percent or more by weight of bicarbonate. In additional instances of this aspect, the bicarbonate solution is added in a volume ratio of from about 0.5 to about 2 times the volume of the liquid, the methanol is added as about 10 to about 50 percent by volume of the volume of the bicarbonate solution, and the heptane is added as about 5 to about 85 percent by volume of the volume of the liquid. That is, the volume of bicarbonate solution added is from about one-half to about twice the volume of the liquid before bicarbonate solution, methanol and heptane addition; the volume of methanol added is about 10 to about 50 percent of the liquid before bicarbonate solution, methanol and heptane addition; and the volume of heptane added is about 5 to about 85 percent of the liquid before bicarbonate solution, methanol and heptane addition. In all instances of this aspect of the first embodiment, all other steps are as described in the general process of the embodiment or in either or both of the first or second aspects of this embodiment.

In a fourth aspect of the first embodiment, step d) comprises adjusting the pH of aqueous layer $A^1$ to a range of from about 2 to about 4 by addition of acid. In this aspect of the first embodiment, all other steps are as described in the general process of the embodiment or in any one or more of the first through third aspects of this embodiment.

In a fifth aspect of the first embodiment, step e) is performed by adding heptane and is conducted at a temperature of from about 15° C. to about 25° C. In particular instances of this aspect, the heptane is added in a volume ratio of from about 0.5 to about 1 times the volume of aqueous layer $A^1$. That is, the volume of heptane added is from about one-half to about the same the volume of aqueous layer $A^1$ before heptane addition. In this aspect of the first embodiment, all other steps are as described in the general process of the embodiment or in any one or more of the first through fourth aspects of this embodiment.

In a sixth aspect of the first embodiment, step f) is performed by addition of an extraction solvent selected from the group consisting of methyl ethyl ketone, ethyl acetate and isopropyl acetate. In particular instances of this aspect, the extraction solvent is added in about a volume ratio of from 0.25 to about 1 times the volume of aqueous layer $A^1$. That is, the volume of extraction solvent added is from about one-half to about the same the volume of aqueous layer $A^1$ before extraction solvent addition. In this aspect of the first embodiment, all other steps are as described in the general process of the embodiment or in any one or more of the first through fifth aspects of this embodiment.

In a seventh aspect of the first embodiment, step g) comprises concentrating the extract to a concentration that is from about 25 to about 65 times an initial concentration of the extract; that is, concentrating the extract to a product concentration in a range of from about 100 to about 150 g/L. In particular instances of this aspect, the concentration is continued until the water level is less than about 1%. In all instances of this aspect, all other steps are as described in the general process of the embodiment or in any one or more of the first through sixth aspects of this embodiment.

In an eighth aspect of the first embodiment, step h) comprises (1) adding isopropyl acetate to the concentrated layer, (2) adding heptane to precipitate the compound of formula I from the concentrated layer, (3) filtering the precipitated compound of formula I, (4) washing the precipitated compound of formula I with heptane, and (5) drying the precipitated compound of formula I under vacuum. In particular instances of this aspect, adding isopropyl acetate results in an isopropyl acetate concentration that is less than about 60%. In this aspect of the first embodiment, all other steps are as described in the general process of the embodiment or in any one or more of the first through seventh aspects of this embodiment.

In a ninth aspect of the first embodiment, step i) comprises crystallizing in methanol. In this aspect of the first embodiment, all other steps are as described in the general process of the embodiment or in any one or more of the first through eighth aspects of this embodiment.

A second embodiment of the invention relates to a process for isolating a compound of formula I:

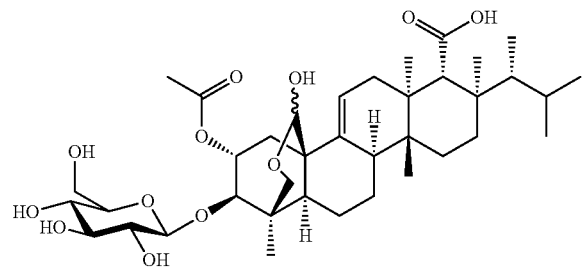

the process comprising:
a) performing solvent extraction on a fermentation broth comprising cells containing a compound of formula I to produce a liquid containing the compound of formula I;
b) removing solids from the liquid;
c) decreasing solvent concentration of the liquid;
d) passing the liquid through a solid phase extraction pretreatment column;
e) decreasing solvent concentration of the liquid;
f) adjusting the pH of the liquid to a range of from about 3.5 to about 4.5;
g) passing the liquid through a solid phase extraction column to capture product fractions containing the compound of formula I;
h) combining the product fractions to produce a combined product fraction containing the compound of formula I;
i) performing solvent extraction to produce an organic layer and an aqueous basic layer containing the compound of formula I;
j) adjusting the pH of the organic layer of step i) to be in a range of from about 2.5 to about 3.5;
k) performing solvent extraction to produce an organic layer containing the compound of formula I and an aqueous acidic layer;
l) concentrating the organic layer of step k) to produce a concentrated layer containing the compound of formula I;
m) adding heptane to the concentrated layer to precipitate the compound of formula I; and n) recrystallizing the precipitate of the compound of formula I from methanol to produce crystals of the compound of formula I.

In a first aspect of the second embodiment, step a) is performed by (1) at a pH in a range of from about 3 to about 8, (2) at a temperature in a range of from about 10° C. to about 50° C., and (3) using a single solvent selected from the group consisting of methanol, ethanol, isopropanol, acetone and acetonitrile. In this aspect of the second embodiment, all other steps are as described in the general process of the embodiment.

In a second aspect of the second embodiment, step a) further comprises adjusting a water to solvent composition ratio of the liquid to about 30 to about 70 percent by volume of solvent. In this aspect of the second embodiment, all other steps are as described in the general process of the embodiment or in the first aspect of this embodiment.

In a third aspect of the second embodiment, step b) comprises removing solids by centrifugation. In this aspect of the second embodiment, all other steps are as described in the general process of the embodiment or in either or both of the first or second aspects of this embodiment.

In a fourth aspect of the second embodiment, step c) comprises decreasing solvent concentration by water addition or by vacuum concentration. In particular instances of the fourth aspect, the water to solvent composition ratio is increased by about 5 to about 20% by volume of solvent. That is, the amount of water present is increased with respect to the amount of solvent present, either by addition of water or by removal of solvent by an appropriate method such as distillation. In all instances of this aspect of the second embodiment, all other steps are as described in the general process of the embodiment or in any one or more of the first through third aspects of this embodiment.

In a fifth aspect of the second embodiment, step d) is performed at a temperature in a range of from about 10° C. to about 35° C. In particular instances of the fifth aspect, an extraction solvent selected from the group consisting of methanol, ethanol, isopropanol, acetone and acetonitrile is used. In particular instances of the fifth aspect, the extraction solvent is acetone. In all instances of this aspect of the second embodiment, all other steps are as described in the general process of the embodiment or any one or more of the first through fourth aspects of this embodiment.

In a sixth aspect of the second embodiment, step e) comprises decreasing solvent concentration by water addition or by vacuum concentration. In particular instances of the sixth aspect, the water to solvent composition ratio is increased by about 5 to about 20% by volume of solvent. That is, the amount of water present is increased with respect to the amount of solvent present, either by addition of water or by removal of solvent by an appropriate method such as distillation. In all instances of this aspect of the second embodiment, all other steps are as described in the general process of the embodiment or any one or more of the first through fifth aspects of this embodiment.

In a seventh aspect of the second embodiment, step f) is performed at a temperature in a range of from about 10° C. to about 35° C. In this aspect of the second embodiment, all other steps are as described in the general process of the embodiment or in any one or more of the first through sixth aspects of this embodiment.

In an eighth aspect of the second embodiment, step g) is performed by (1) washing the solid phase extraction column with a solvent comprising about 30 percent by volume of acetone; (2) washing the solid phase extraction column a solvent comprising about 40 percent by volume of acetone; and (3) eluting the compound of formula I from the solid phase extraction column with a solution comprising about 60 percent by volume of acetone in sodium bicarbonate solution. In this aspect of the second embodiment, all other steps are as described in the general process of the embodiment or in any one or more of the first through seventh aspects of this embodiment.

In a ninth aspect of the second embodiment, step i) further comprises (1) washing the combined product fraction with a first solution of heptane and isopropyl acetate to produce an aqueous layer and an organic layer; (2) removing the aqueous layer from the organic layer; (3) adjusting the pH of the aqueous layer of (2) to a range of about 8.25 to about 9.25; (4) washing the aqueous layer of (2) with a second solution of heptane and isopropyl acetate to produce an aqueous layer and an organic layer; and (5) removing the aqueous layer of (5) from the organic layer of (5). In this aspect of the second embodiment, all other steps are as described in the general process of the embodiment or in any one or more of the first through eighth aspects of this embodiment.

In a tenth aspect of the second embodiment, step j) comprises adjusting the pH of the aqueous layer of step i) to a range of about 2.75 to about 3.25. In this aspect of the second embodiment, all other steps are as described in the general process of the embodiment or in any one or more of the first through ninth aspects of this embodiment.

In an eleventh aspect of the second embodiment, step j) is conducted at a temperature of from about 15° C. to about 25° C. In this aspect of the second embodiment, all other steps are as described in the general process of the embodiment or in any one or more of the first through tenth aspects of this embodiment.

In a twelfth aspect of the second embodiment, step k) comprises adding isopropyl acetate to the aqueous layer of step j) to extract the compound of formula I into the organic layer. In particular instances of this aspect, step k) is conducted at a temperature of from about 10° C. to about 35° C. In all instances of this aspect of the second embodiment, all other steps are as described in the general process of the embodiment or in any one or more of the first through tenth aspects of this embodiment.

In a thirteenth aspect of the second embodiment, step l) comprises concentrating the organic extract to about 40 g/L. In this aspect of the second embodiment, all other steps are as described in the general process of the embodiment or in any one or more of the first through eleventh aspects of this embodiment.

The present invention also includes compounds prepared using the processes of the claimed method and their use as antifungal agents. See Fernando Peláez et al., *The Discovery of Enfumafungin, a Novel Antifungal Compound Produced by an Endophytic Hormonema Species Biological Activity and Taxonomy of the Producing Organisms*, 23 SYSTEM. APPL. MICROBIOL. 333 (2000); WO2007/127012; WO2007/126900; WO2009/045311. In these uses, such compounds can optionally be employed in combination, either sequentially or concurrently, with one or more therapeutic agents effective against fungal/bacterial infections.

Isolation and Purification of Enfumafungin

Enfumafungin is a natural product produced from a strain of *Hormonema carpetanum*, MF 6176 in the culture collection of Merck & Co., Inc., Rahway, N.J., which has been deposited under the Budapest Treaty in the culture collection of the American Type Culture Collection on Jan. 23, 1996, at 12301 Parklawn Drive, Rockville, Md. 20852 and assigned accession number ATCC 74360. Although the invention is discussed principally with respect to the specific strain, it is well known in the art that the properties of microorganisms can be varied naturally and artificially. Thus, all strains derived from *Hormonema carpetanum* MF 6176, ATCC 74360 including varieties, mutants and other microorganisms producing enfumafungin, whether obtained by natural selection, produced by the action of mutating agents, such as ionizing radiation or ultraviolet irradiation, or by the action of chemical mutagens, such as nitrosoguanidine, can be used as a source for producing enfumafungin, which is purified as described herein.

GENERAL PROCEDURES

Procedure 1

Culture of *Hormonema* sp.

*Hormonema* sp. MF 6176, ATCC 74360, may be cultured in a suitable nutrient medium, including those described in U.S. Pat. No. 5,756,472. Tables presenting representative suitable solid and liquid media, including a representative seed medium, are reproduced herein as Tables 1-3.

TABLE 1

| KF SEED MEDIUM | | Trace Element Mix | |
|---|---|---|---|
| | per liter | | per liter |
| Corn Steep Liquor | 5 g | $FeSO_4 \cdot 7 H_2O$ | 1 g |
| Tomato Paste | 40 g | $MnSO_4 \cdot 4 H_2O$ | 1 g |
| Oat flour | 10 g | $CuCl_2 \cdot 2 H_2O$ | 25 mg |
| Glucose | 10 g | $CaCl_2$ | 100 mg |
| Trace Element Mix | 10 ml | $H_3BO_3$ | 56 mg |
| pH = 6.8 | | $(NH_4)_6Mo_7O_{24} \cdot 4 H_2O$ | 19 mg |
| | | $ZnSO_4 \cdot 7 H_2O$ | 200 mg |

TABLE 2

| SOLID PRODUCTION MEDIUM | |
|---|---|
| Component | per 250 ml flask |
| Brown Rice | 10 g |
| Yeast Extract | 20 mg |
| Sodium Tartrate | 10 mg |
| $KH_2PO_4$ | 10 mg |
| Distilled Water | 20 ml |

The pH was not adjusted prior to autoclaving for 20 minutes.

Immediately before use, the medium was moistened with 15 ml of distilled water and autoclaved again for 20 minutes.

TABLE 3

| LIQUID PRODUCTION MEDIUM | |
|---|---|
| Component | per liter |
| Glucose | 50 g |
| Tryptophan | 1 g |
| Fidco-Yeast Extract | 10 g |
| NZ-Amine (type E) | 33 g |
| Ammonium Sulfate | 5 g |
| $KH_2PO_4$ | 9 g |

The pH was adjusted to 6.2 with NaOH before autoclaving.

Generally, the culture is first grown in a seed medium and the culture growth then used to inoculate a production medium. The production medium may be a solid medium or a liquid medium. In a representative culture, vegetative mycelia of the culture are prepared by inoculating 54 ml of seed medium (Table 1) in a 250 ml unbaffled Erlenmeyer flask with 2 ml of mycelia in 10% glycerol that had been stored at −80° C. Seed cultures are incubated for 3 days at 25° C. and 85% relative humidity on a rotary shaker with a 5 cm throw at 220 rpm in a room with constant fluorescent light. 2 ml portions of the culture are used to inoculate a second stage seed culture and further incubated for 3 days with the conditions noted above. 2 ml portions of this 3-day culture are used to inoculate 50 ml portions of the liquid production medium (Table 3) or solid rice-based production medium (Table 2) in 250 ml unbaffled Erlenmeyer flasks.

The crude culture of cells (whole broth) is used in the purification methods described below.

Procedure 2: Enfumafungin Isolation

First Embodiment

Extraction of Enfumafungin from Fermentation Broth

The isolation of Enfumafungin begins with a solvent extraction to remove the product from the fermentation broth. This extraction is accomplished using a combination of solvents. A combination solvent extraction uses a main solvent accompanied by a co-solvent, which represents from about 0 to about 25 percent by volume (volume percent or vol %) of the total solvent volume. The main solvents that can be used in a combination solvent extraction are methyl ethyl ketone (MEK), isobutanol, ethyl acetate (EtAc), isopropyl acetate (IPAc or IPAC), while co-solvents include methanol (MeOH), ethanol (EtOH), isopropanol, acetone, and acetonitrile. The pH of the extraction ranges from about 3 to about 8 while the temperature ranges from 10 to 40° C. The solvent to whole broth ratio ranges from about 0.8 to about 1.2.

Crude Isolation.

The spent cell solids from the solvent extraction are separated using centrifugation. If a water immiscible solvent is used for the extraction (either alone or in combination with another solvent), then the aqueous layer is discarded with the spent cell solids during centrifugation. The extract is concentrated to a volume that is reduced from about 5 to about 25 times the original volume using vacuum distillation to remove water and allow for smaller processing volumes. The product concentration should not exceed about 10 g/L.

The product is extracted into an aqueous phase by the addition of about 5 or more percent by weight (wt %) of bicarbonate solution (about 0.5 to about 2 volume ratio to extracted liquid), methanol (about 10 to about 50 volume percent of the bicarbonate solution volume), and heptane (about 5 to about 85 volume percent of the volume of the extracted liquid) and mixed for at least 30 minutes. Any combination of n-heptanes can be substituted for heptane for any extraction or precipitation step in this isolation. The aqueous layer, containing the product, is cut from the organic layer, and pH adjusted between about 2 to about 4 using an acid solution. The organic layer containing impurities is discarded.

Heptane (about 0.25 to about 1 volume) is added to the acidic product layer at a temperature of from about 15° C. to about 25° C. and mixed for at least 30 minutes. The heptane layer is cut away from the aqueous product layer. The product is subsequently extracted into an organic phase at a temperature of from about 15° C. to about 25° C. by adding a solvent (about 0.25 to about 1 volume) from one of the following solvents: ethyl acetate, isopropyl acetate, and MEK. The resulting spent aqueous phase containing polar impurities is then discarded.

The resulting organic extract is concentrated using vacuum distillation to a product concentration range of from about 100 to about 150 g/L. Isopropyl acetate (from about 10 to about 80 volume percent) is added to the concentrate at a temperature of from about 35° C. to about 55° C. to prevent the product from oiling out of solution during the heptane addition. Heptane (from about 5 to about 85 volume percent) is added to precipitate the product and acts as an antisolvent. The product solids are filtered, washed with heptane, and dried under vacuum. The solid purity ranges from about 30 to about 70 wt %.

Crystallization.

The crystallization process involves dissolving the solids from the crude isolation protocol in methanol to a concentration of from about 120 to about 160 g/L at about 50° C. The addition of seed (from about 0 to about 1 wt %) can be employed but is optional. The solution is cooled to about 20° C. over about 2 to about 4 hours and held at about 20° C. for about 1 hour. The slurry is heated back to about 50° C. over about 15 to about 60 minutes and held at about 50° C. for about 30 minutes. This temperature ramp is repeated at least two more times. When the temperature ramp is finished, the slurry is cooled to a temperature between about −5 and about −15° C. over about 2 to about 4 hours and held at this temperature for at least 1 hour. The product crystals are filtered, washed with methanol, and dried under vacuum. The solid purity and yield ranges from about 90 to about 99 wt % and from about 65 to about 80% respectively. The level of analog impurity is reduced in this crystallization to less than about 2 Å % by HPLC analysis.

Procedure 3: Enfumafungin Isolation

Second Embodiment

Extraction of Enfumafungin

The isolation of Enfumafungin begins with a solvent extraction to produce a liquid containing the compound of formula I. This extraction is accomplished using a single solvent. The following solvents are used to extract the product: methanol, ethanol, isopropanol, acetone, and acetonitrile. The solvent to water composition is dependent on the solvent selected. A typical solvent used for the extraction is acetone with a water to solvent composition of about 45 volume percent, i.e., about 45% water and about 55% acetone. The pH of the extraction ranges from about 3 to about 8, while the temperature ranges from about 10° C. to about 50° C. Insoluble solids are then removed by centrifugation.

Crude Isolation.

After removal of the solids, then the water to solvent composition is adjusted from about 45 to about 50 volume percent of solvent (for example, from about 48 to about 52 volume percent) and passed through a solid phase extraction pretreatment column at a temperature of from about 10° C. to about 35° C. This pretreatment column is used to remove impurities that are more non-polar than the compound of formula I from the extract. The pretreated extract is concentrated using a vacuum distillation to a water to solvent composition range of from about 65 to about 75 volume percent. Alternately, water can be added to achieve the same composition. The pH of the concentrate is adjusted between about 3.5 to about 4.5 with acid and passed through a solid phase extraction column in capture mode at a temperature of from about 10° C. to about 35° C. (from about 139 to about 554 cm/hr, from about 3 to about 13 g/L loading). After loading, the column is washed with from about 2 to about 4 column volumes (CVs) of about 30 volume percent of acetone and from about 2 to about 4 CVs of about 45 volume percent of acetone. The product is eluted with from about 3 to about 6 CVs of about 60 volume percent of acetone in sodium bicarbonate solution. The column is regenerated with from about 2 to about 4 CVs of 80 volume percent or 100 volume percent of acetone.

The product fractions from the capture column are pooled together. If non-polar impurities are present in the pooled product fractions, these fractions are pH adjusted between about 4 and about 7 with acid and washed with about 90 volume percent of heptane/about 10 volume percent of isopropyl acetate (from about 0.5 to about 1 volume of wash) at a temperature of from about 10° C. to about 35° C. The aqueous product layer is cut from the organic layer and adjusted to a pH range of from about 8.25 to about 9.25 using base. The product layer is washed with about 75 volume percent of isopropyl acetate/about 25 volume percent of heptane (from 0.5 to 1 volume of wash) at a temperature of from about 10° C. to about 35° C. The aqueous product layer is cut from the organic layer and adjusted to a pH range of from about 2.5 to about 3.5 using acid. The product is extracted from the aqueous layer by the addition of isopropyl acetate (from about 0.5 to about 1 volume) at a temperature of from about 10° C. to about 35° C. The organic extract is concentrated to about 40 g/L and from about 0 to about 30 volume percent of heptane is added to complete precipitation of the product. The product solids are filtered, washed with heptane, and dried under vacuum. The solid purity ranges from about 50 to about 85 wt %.

Crystallization.

The crystallization method involves dissolving the solids from the second crude isolation in methanol to a concentration of from about 70 to about 100 g/L at about 55° C. Add seed (from about 0 to about 3 wt %) to the solution. The slurry is cooled to about 25° C. over at least 1 hour. The slurry is concentrated by vacuum to a concentration of from about 140 to about 160 g/L. After concentration, the slurry is cooled to a temperature of from about 4° C. to about 10° C. and aged for at least 12 hours. The product crystals are filtered, washed with methanol, and dried under vacuum. The solid purity ranges from about 90 to about 99 wt %.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for isolating a compound of formula I:

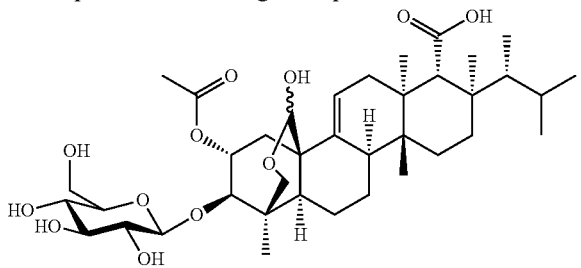

the process comprising:
a) performing solvent extraction on a fermentation broth comprising cells containing a compound of formula I to produce an organic liquid containing the compound of formula I;
b) concentrating the organic liquid containing the compound of formula I;
c) performing solvent extraction on the concentrated liquid to produce aqueous layer A1 containing the compound of formula I;
d) adjusting the pH of aqueous layer $A^1$ to a range of from about 2 to about 4 by addition of acid;
e) adding heptane to aqueous layer $A^1$ and removing the heptane layer;
f) performing solvent extraction on aqueous layer $A^1$ to produce organic layer $O^2$ containing the compound of formula I and aqueous layer $A^2$;
g) concentrating organic layer $O^2$ to produce a concentrated layer containing the compound of formula I;
h) precipitating the compound of formula I from the concentrated layer; and
i) crystallizing the precipitated compound of formula I.

2. The process according to claim 1, wherein said step a) is performed using a combination solvent consisting of 100 to about 75 percent by volume of a main solvent and 0 to about 25 percent by volume of a co-solvent; said main solvent chosen from the group consisting of methyl ethyl ketone, isobutanol, ethyl acetate and isopropyl acetate, and said co-solvent chosen from the group consisting of methanol, ethanol, isopropanol, acetone and acetonitrile.

3. The process according to claim 1, wherein said step a) is performed at a pH in a range of from about 3 to about 8 and a temperature in a range of from about 10° C. to about 40° C.

4. The process according to claim 1, wherein said step c) is performed adding bicarbonate solution comprising 5 percent or more by weight of bicarbonate, methanol and heptane.

5. The process according to claim 4, wherein:
(1) said bicarbonate solution is added in a volume ratio of from about 0.5 to about 2 times the volume of said liquid,
(2) said methanol is added as about 10 to about 50 percent by volume of the volume of said bicarbonate solution, and
(3) said heptane is added as about 5 to about 85 percent by volume of the volume of said liquid.

6. The process according to claim 1, wherein step e) is conducted at a temperature of from about 15° C. to about 25° C. and said heptane is added in a volume ratio of from about 0.25 to about 1 times the volume of aqueous layer $A^1$.

7. The process according to claim 1, wherein said step f) is performed by addition of an extraction solvent selected from the group consisting of methyl ethyl ketone, ethyl acetate and isopropyl acetate.

8. The process according to claim 7, wherein said extraction solvent is added in a volume ratio of from about 0.25 to about 1 times the volume of aqueous layer $A^1$.

9. The process according to claim 1, wherein said step h) comprises:
(1) adding isopropyl acetate to the concentrated layer,
(2) adding heptane to precipitate the compound of formula I from the concentrated layer,
(3) filtering the precipitated compound of formula I,
(4) washing the precipitated compound of formula I with heptane, and
(5) drying the precipitated compound of formula I under vacuum.

10. The process according to claim 1, wherein said step i) comprises crystallizing in methanol.

11. A process for isolating a compound of formula I:

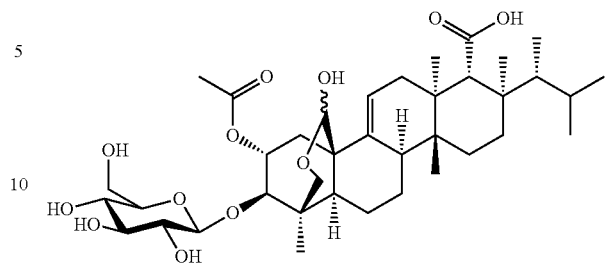

the process comprising:
a) performing solvent extraction on a fermentation broth comprising cells containing a compound of formula I to produce a liquid containing the compound of formula I using a single solvent selected from the group consisting of methanol, ethanol, isopropanol, acetone and acetonitrile;
b) removing solids from the liquid;
c) decreasing solvent concentration of the liquid;
d) passing the liquid through a solid phase extraction pretreatment column using an extraction solvent selected from the group consisting of methanol, ethanol, isopropanol, acetone and acetonitrile;
e) decreasing solvent concentration of the liquid;
f) adjusting the pH of the liquid to a range of from about 3.5 to about 4.5 using an extraction solvent selected from the group consisting of methanol, ethanol, isopropanol, acetone and acetonitrile;
g) passing the liquid through a solid phase extraction column to capture product fractions containing the compound of formula I;
h) combining the product fractions to produce a combined product fraction containing the compound of formula I;
i) performing solvent extraction to produce an organic layer and an aqueous layer containing the compound of formula I;
j) adjusting the pH of the organic layer of step i) to be in a range of from about 2.5 to about 3.5;
k) performing solvent extraction to produce an organic layer containing the compound of formula I and an aqueous layer;
l) concentrating the organic layer of step k) to produce a concentrated layer containing the compound of formula I;
m) adding heptane to the concentrated layer to precipitate the compound of formula I; and
n) recrystallizing the precipitate of the compound of formula I from methanol to produce crystals of the compound of formula I.

12. The process according to claim 11, wherein step a) further comprises adjusting a water to solvent composition ratio of the liquid to about 30 to about 70 percent by volume of solvent.

13. The process according to claim 11, wherein step b) comprises removing solids by centrifugation.

14. The process according to claim 11, wherein step c) comprises decreasing solvent concentration by water addition or vacuum concentration.

15. The process according to claim 11, wherein the extraction solvent in step d) is acetone.

16. The process according to claim 11, wherein step e) comprises decreasing solvent concentration by water addition or vacuum concentration.

17. The process according to claim 11, wherein the extraction solvent in step f) is acetone.

18. The process according to claim 11, wherein step h) comprises:
   (1) washing the solid phase extraction column with a solvent comprising about 30 percent by volume of acetone;
   (2) washing the solid phase extraction column a solvent comprising about 40 percent by volume of acetone; and
   (3) eluting the compound of formula I from the solid phase extraction column with a solution comprising about 60 percent by volume of acetone in sodium bicarbonate solution.

19. The process according to claim 11, wherein step i) further comprises:
   (1) washing the combined product fraction with a first solution of heptane and isopropyl acetate to produce an aqueous layer and an organic layer;
   (2) removing the aqueous layer from the organic layer;
   (3) adjusting the pH of the aqueous layer to a range of about 8.25 to about 9.25;
   (4) washing the aqueous layer with a second solution of heptane and isopropyl acetate to produce an aqueous layer and an organic layer; and
   (5) removing the aqueous layer of step (4) from the organic layer of step (4).

20. The process according to claim 11, wherein step j) comprises:
   (1) adjusting the pH of the aqueous layer of step i) to a range of about 2.75 to about 3.25; and
   (2) adding isopropyl acetate to the aqueous layer of step (2) to extract the compound of formula I into the organic extract.

\* \* \* \* \*